United States Patent [19]
Iund et al.

[11] Patent Number: 5,598,840
[45] Date of Patent: Feb. 4, 1997

[54] APPARATUS AND METHOD FOR VENTILATION AND ASPIRATION

[75] Inventors: Neal A. Iund, Centerville; Francine B. Petersen, Bountiful; Peter W. H. Coles, Salt Lake City; James L. Sorenson, Salt Lake City; Reed F. Winterton, Salt Lake City, all of Utah

[73] Assignee: Sorenson Critical Care, Inc., Salt Lake City, Utah

[21] Appl. No.: 405,588

[22] Filed: Mar. 17, 1995

[51] Int. Cl.$^6$ ............................ A61M 1/00; A61M 39/00
[52] U.S. Cl. ................. 128/207.14; 128/207.16; 128/202.27; 604/163
[58] Field of Search .............. 128/207.14–207.17, 128/202.27, 205.19, 200.26; 604/118, 119, 163, 171, 110, 111

[56] References Cited

U.S. PATENT DOCUMENTS

| | | | |
|---|---|---|---|
| 4,836,199 | 6/1989 | Palmer | 128/207.16 |
| 4,967,743 | 11/1990 | Lambert | 128/202.16 |
| 5,088,486 | 2/1992 | Jinotti | 128/207.14 |
| 5,139,018 | 8/1992 | Brodsky et al. | 128/207.14 |
| 5,220,916 | 6/1993 | Russo | 128/207.16 |
| 5,279,549 | 1/1994 | Ranford | 604/34 |
| 5,309,902 | 5/1994 | Kee et al. | 128/202.27 |

FOREIGN PATENT DOCUMENTS

91/01771   2/1991   WIPO ................ 128/207.14

*Primary Examiner*—V. Millin
*Assistant Examiner*—Eric P. Raciti
*Attorney, Agent, or Firm*—Trask, Britt & Rossa

[57] ABSTRACT

A sealed ventilation circuit interface system, which enables simultaneous patient ventilation and safe tracheal suctioning, is structured to accommodate any of a wide variety of commercially available suction catheters. The interface system comprises a manifold assembly, and an adaptor. The manifold assembly may be attached to a patient for an extended period, while the adaptor is advantageously constructed as a single procedural use disposable device. The adaptor couples with the manifold assembly, and may be configured to effect the introduction of a catheter through a normally closed valve structure carried by the manifold assembly. The adaptor may alternatively be configured to interface the manifold with a bronchoscope or other appliance. A vacuum valve assembly biased in an open position is selectively actuated between open and closed positions and can be locked in a closed position. The vacuum valve remains at either position without ongoing manual pressure.

18 Claims, 8 Drawing Sheets

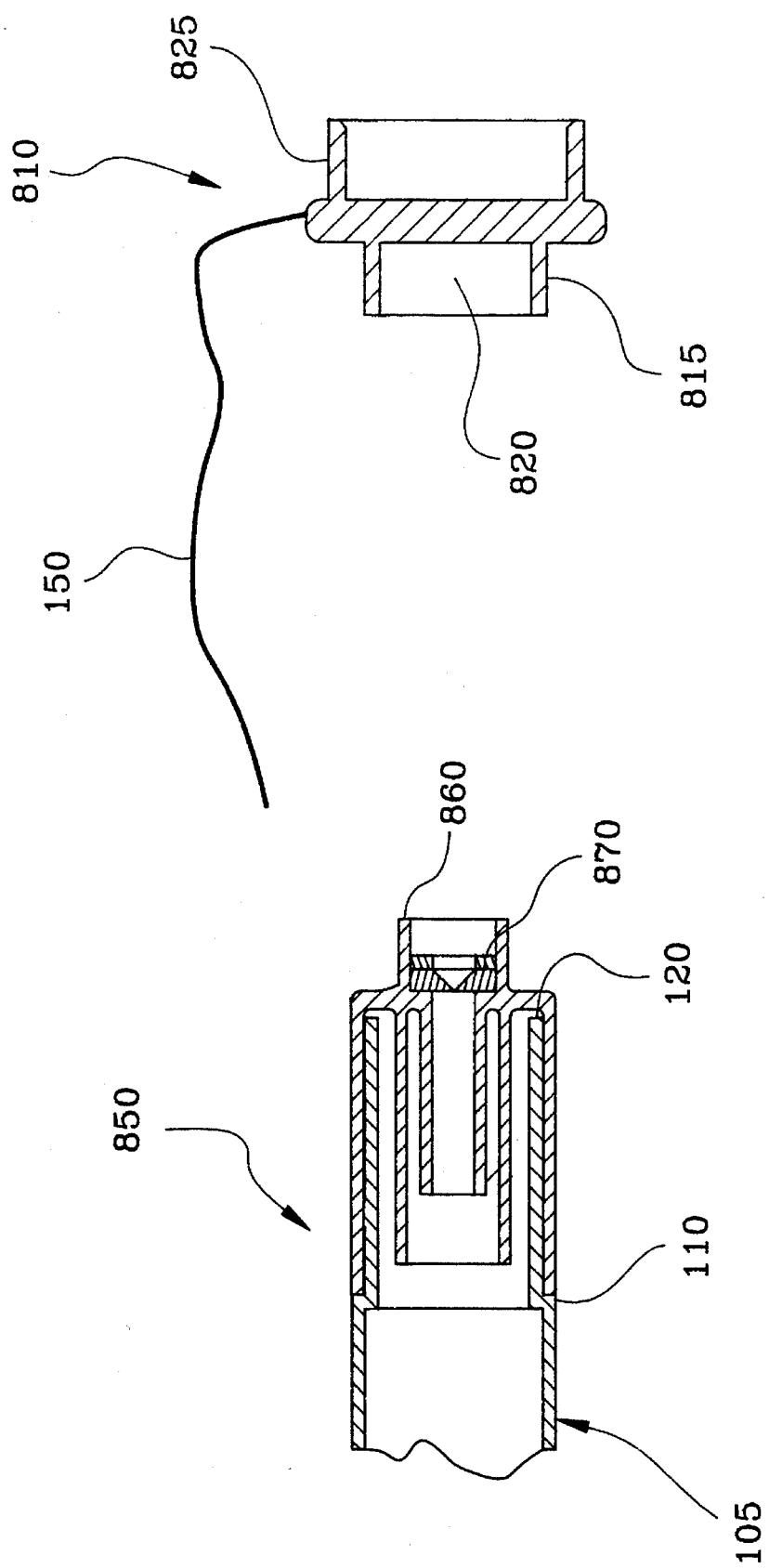

APPARATUS AND METHOD FOR VENTILATION AND ASPIRATION

BACKGROUND OF THE INVENTION

1. Field

This invention relates to means for ventilating and aspirating the respiratory tracts of medical patients. It is particularly directed to an improved ventilation circuit interface system, catheter assembly and suction valve.

2. State of the Art

Interface systems for endotracheal suctioning and ventilating virtually all include a manifold structure enabling introduction of ventilating gases and intermittent exhalation of patient breath simultaneously with insertion and option of a tracheal suctioning catheter. These interface systems generally also include some means for selectively communicating a vacuum source the suctioning catheter. Almost universally, these systems involve at least one collapsible, plastic envelope entirely surrounding the catheter and purporting to provide a sterile barrier between the otherwise exposed external surface of the catheter and the ambient atmosphere. In practice, a practitioner manually externally collapses the envelope onto the external surface of the catheter and advances the catheter into the trachea of a patient, retracting the catheter in a similar fashion following the aspiration procedure.

These close-system devices under present medical protocol are ordinarily used at least hourly for up to 48 hours for each patient before being replaced. Problems attendant to such frequent and repeated in-dwelling use are numerous, including, among other problems, constriction of the catheter lumen and valve flow path with undesired respiratory secretions, some of which thicken with age, creation of contaminant-passing pinholes in the collapsible plastic barrier and the need to physically move the lengthy and cumbersome devices from one location on the body of the patient to another when the devices interfere with other procedures. Associated with the dried and drying secretions inside the lumen, are like secretions on the exterior of the catheter wall which accumulate at the manifold wiper seal. Such thick and undesired respiratory secretions not only restrict the facile movement of the catheter through the manifold, but also can be unavoidably reintroduced to the patient in subsequent repeat procedures.

Structures and methods descriptive of the current state of the art are described, among other places, in U.S. Pat. Nos. 5,333,606 to Schneider et al.; U.S. Pat. No. 5,025,806 to Palmer et al.; U.S. Pat. No. 4,850,350 to Jackson; U.S. Pat. No. 4,588,160 to Flynn et al.; U.S. Pat. No. 4,453,295 to Laszczower; and U.S. Pat. No. 4,351,328 to Bodai.

The foregoing patents collectively disclose methods and apparatus for performing endotracheal suctioning procedures on a medical patient without the need for disconnecting the patient from a respirator. During such procedures, positive end expiratory pressure is maintained without interruption during suctioning and with notable ease of catheter removal from an associated ventilation manifold. These patents include description of structures for selectively constricting the fluid flow path within the catheter lumen by manual compression of a tube clamping device.

There remains a need for a ventilating and aspirating device, wherein a single-patient, single-use suction catheter may be releasably coupled at its distal (patient) end to a single-patient, multiple-use manifold and may be releasably coupled at its proximal (user) end with a multiple-patient, multiple-use valve.

Also, a need remains for a tracheal suctioning device which accommodates alternative means of protecting a user from exposure to contamination from the external surface of the suctioning catheter.

A further need remains for a reusable valve structure which can be selectively locked in a closed position yet be readily mechanically actuated between an open position and a closed position without exertion of ongoing manual pressure to maintain the valve in either position.

SUMMARY OF THE INVENTION

The present invention provides an improved apparatus and method for simultaneously ventilating and aspirating respirator secretions of a medical patient. It may be embodied as an assemblage of individually unique components. Each of these components may be beneficially incorporated individually in existing ventilation circuit systems, but their combination is particularly advantageous. The major components of this invention include (1) an improved ventilation circuit interface, comprising a sealed ventilation circuit manifold assembly that enables simultaneous patient ventilation and protected facile tracheal suctioning, (2) a suctioning catheter assembly which may be releasably coupled at the proximal end to a valve and at the distal end to a manifold, wherein the catheter is optionally enveloped by a sterility enhancing protective barrier and (3) an improved vacuum valve.

A catheter assembly of the invention is ideally coupled to a manifold component of this invention through an adaptor, which may be a component of either of the manifold or catheter assemblies. The adaptor may be structured to create a sealed sliding interface between a catheter and the manifold. An adaptor may alternatively be embodied to accommodate other appliances, thereby enabling alternate therapeutic or diagnostic procedures, e.g., bronchoscopies and the infusion of nebulized medicaments through the manifold. A plurality of alternatively structured such adapters may be provided in association with a single manifold.

Though the adaptor may be an integral dement of a manifold component, currently preferred embodiments of the interface system of this invention provide the adaptor as a separate component, typically a catheter adaptor, of a manifold assembly. The manifold assembly will ordinarily be attached to a patient for an extended period, typically 24–72 hours. The catheter adaptor may be constructed as either a single or multiple procedural use disposable device; it is ideally constructed to accept interchangeably a variety of commercially available catheters. Catheters with flared tips and obvious depth markings are presently considered to be most useful. In any case, the distal end of the catheter robe is structured to permit respiratory secretions to be drawn into the lumen of the catheter robe.

The invention enables a practitioner to insert a flexible catheter tube into a region on either side of the carina of a patient in one smooth motion with minimal risk of contamination or infection and without assistance from others. Additionally, a practitioner is able selectively to inactivate and activate vacuum pressure through a vacuum vane assembly with either hand and without assistance from others.

The catheter assembly comprises, in certain embodiments, a standard flexible tracheal suctioning catheter tube attached at the user end to a proximal coupling and at its opposite end to a distal coupling. Each of these couplings may be configured to enhance the effectiveness of finger actuation for releasably coupling opposite ends of the catheter assembly to the vacuum valve assembly and to an adaptor. The outer surface of a coupling may be configurated, as by knurling. Alternatively, the body of the coupling may be non-cylindrical or otherwise fashioned as a wing coupling. The term "wing coupling" is intended to include any coupling structure which includes radial extensions, either inherent in its cross sectional configuration, or otherwise comparable to those of a conventional "wing nut." It is also within contemplation to color code the respective couplings in coordination with similar colors applied to the manifold and/or valve components. Color indicators of this type are of assistance to proper assembly.

The catheter assembly of preferred embodiments additionally comprises a collapsible bag enveloping the suctioning catheter tube and attached to the proximal and distal couplings. The collapsible bag may be attached to the exterior periphery of the couplings by any suitable means, such as an adhesive, tape, a shrink band or a molded band. The bag is formed preferably of vinyl, polyurethane or PET such as MYLAR®, or less preferably of polyethylene. The catheter tube is slidable lengthwise through a passageway in a multi-function manifold positioned at the distal end of the apparatus. The manifold preferably includes a port at the distal end for attachment to and communication with an indwelling intubation device, such as a tracheostomy tube, endotracheal tube or nasopharyngeal tube. The manifold also preferably includes a ventilating structure extending radially from and in fluid communication with the passageway, for selectively introducing ambient air, oxygenated air and other therapeutic gasses into the respiratory system of the patient. Other conduits may also be provided for the introduction of other suitable gases and lavage solutions to the respiratory system.

This invention ideally includes an advantageous ventilation circuit interface system for interfacing a suction catheter with an intubation device. The interface system may, in its preferred embodiment, be visualized as comprising two major components: specifically, a manifold assembly and a catheter adaptor. In practice, the adaptor may be associated in a package or kit with one or more catheters. Alternatively, a manifold assembly may be associated with a plurality of catheter adapters.

The manifold generally has a body with an open interior. A distal end portion of the body is adapted to couple with an intubation device. A proximal end portion of the body is formed as an open port defined by a continuous wall. The manifold may take various forms, but its proximal end portion should be approximately axially aligned with its distal end portion so that a catheter may be inserted through the proximal end portion to exit from the distal end portion. In the preferred embodiment, a directional barrier is carried by the proximal end portion of the manifold assembly. It is constructed and arranged to effect a seal against fluid flow through the open interior of the manifold towards the proximal end portion but to pass a catheter introduced through the proximal end portion.

Preferably, the directional barrier is configured to be inserted in the proximal end portion in sealing relationship with the open interior, and comprises a normally closed valve structure. The normally closed valve structure may be constructed and arranged to effect a sliding seal arrangement with the external surface of a catheter passed through the body of the manifold; that is, from the proximal end portion towards the distal end portion through the valve structure.

Preferably, the valve and catheter adaptor are mutually adapted to effect this sliding seal. The valve structure may carry detection means constructed and arranged to signal the precise location of the tip of a catheter positioned within the valve structure. For example, this means may signal, by resistance to travel or sound, the presence of the tip when it is moved to the proximity of the valve structure from a location closer to the distal end portion of the manifold assembly.

An alternative embodiment of the invention comprises a catheter adaptor as previously described, but with no valve structure. Yet a further alternative embodiment of the invention comprises a manifold with neither a valve structure nor a catheter adaptor; rather this further alternative embodiment comprises a manifold closed at its proximal end except for an entry essentially axially concentric with the body of the manifold. The entry is constructed and arranged to effect a sliding seal with the exterior surface of a removable, single-use catheter.

The manifold assembly desirably includes a ventilation port in fluid flow communication with the open interior of the manifold body. The central axis of the ventilation port will ordinarily be oriented transverse the central axes of the proximal end portion and the distal end portion of the manifold. A lavage port may also be provided in fluid flow communication with the open interior. The central axis of the lavage port should also be oriented transverse the central axes of the proximal end portion and the distal end portion.

The catheter adaptor typically includes a leading end portion adapted to couple with the proximal end portion of the manifold and a trailing end portion carrying a catheter introducer structure. The introducer structure is constructed and arranged to interface with the directional barrier when the leading end portion of the adaptor is coupled with the proximal end portion of the manifold. For example, it may comprise an introducer tip constructed as a continuous wall to define an interior passageway configured to receive and pass a catheter and an exterior surface configured to interface with the directional barrier. The directional barrier is further preferably structured to effect a resilient seal against an internal surface of the continuous wall. The interior passageway may include an entry constructed and arranged to effect a sliding seal with the exterior surface of a catheter. In any event, the exterior surface of the introducer tip and the directional barrier are mutually adapted to effect a sealed relationship when the leading end portion of the catheter adaptor is coupled with the proximal end portion of the manifold body.

The directional barrier may be structured to effect a resilient seal both against an internal surface of the open interior of the manifold body and between the proximal end portion of the manifold body and the catheter adaptor.

A fluid collector may be carded by the trailing end portion of the catheter adaptor. This collector functions to accumulate sputum fluids and the like wiped from a catheter as it is withdrawn through the barrier seal. In one embodiment, the collector includes a chamber positioned in approximate axial alignment with the distal end portion opposite the manifold with respect to the leading end portion. A proximal closing member for the chamber carries an entry approximately axially aligned with the introducer tip. The closing member may be structured to effect a sliding seal with the exterior surface of a catheter.

The chamber is desirably structured as a hollow cylindrical extension from the trailing end portion of the adaptor. The closing member is desirably structured as an end panel of the extension with a central opening adapted to receive a catheter in friction-slipping engagement. The term "friction slipping," as used in this disclosure, refers to a slidable association in which the exterior surface of the catheter is engaged about its circumference by the interior surface of the central opening of the end panel. Fluids adhering to the catheter are thus removed by a wiping action as the catheter is withdrawn through the opening. The end panel conveniently comprises a removable cap structured and arranged to effect a sealed closure of the cylindrical extension.

In use, the manifold assembly is interposed between a patient's indwelling tube at the distal end of the manifold and a ventilating circuit. These junctions preferably embody a swivel configuration to permit left or fight bedside placement of the ventilation circuitry, and free rotation of the ventilation circuit with patient head movement to reduce the risk of extubation.

The directional barrier may be configured as an elongate pressure and sterility barrier, and the opening of the normally closed valve may be in the shape of a duckbill or cross, with a normally closed central aperture interposed within the passageway of the manifold. Whether the barrier is structured to include an aperture of elongate transverse dimension or a simple slit in a membranous end of the barrier wall, the barrier in combination with the adaptor assembly provides an effective seal against patient expectoration, contaminant migration and pressure leakage.

The catheter adaptor may be configured as an adaptor assembly surrounding the catheter, including an introducer tip and a concentric outer introducer housing connected at one end by an adaptor base. The introducer housing fits snugly over the outside of the proximal end of the manifold. As the introducer housing is slid over the manifold, first coupling structure carried by the external surface of the manifold engages second coupling structure associated with the internal wall of the introducer housing. The first and second coupling structures are mutually adapted to allow the practitioner to slide the adaptor assembly and manifold toward one another until the manifold is sealed against the adaptor base. Then the housing is rotated with respect to the manifold at a first position positively to lock the adaptor and manifold together during use of the device.

The introducer housing may be slid over the proximal end of the manifold near a second position. An initial sterile barrier is thereby created. After the initial barrier is created, the introducer housing is further slid toward the manifold to the first position, causing the introducer tip to penetrate the aperture of the directional barrier. Though this penetration may preliminarily partially compromise the aperture seal, the initial sterile barrier between the manifold and introducer housing maintains a closed-system environment within the manifold. After the introducer tip has penetrated the directional barrier, the catheter can be advanced, with minimal frictional resistance, through the manifold and indwelling tube into either the trachea of the patient.

Once the catheter and adaptor are attached to the manifold, a presuction saline lavage is typically introduced through the lavage port into the manifold. The lavage loosens tracheal and bronchial secretions, thereby facilitating their removal through the distal end of the manifold. The lavage port is purposefully located immediately adjacent to the patient tube and with a fluid injection angle transverse the longitudinal axis of the manifold so as to optimally direct the saline flow into the patient tube with little risk of back flow into the ventilation circuit. One preferred manifold design incorporates a window through which a practitioner may view the catheter, its contents and any depth markings which may be printed on the catheter.

While the practitioner is performing the evacuation procedure, the catheter may be repeatedly inserted and retracted with selective introduction of lavage fluid through a lavage port on the manifold. The manifold is configured to prevent lavage fluid from draining through the ventilation port, obviating the need for the manifold to be tilted during lavage and thereby averting the potential for disconnection of the manifold from the indwelling endotracheal tube.

Upon repeated advancement and retraction of the catheter during an evacuation procedure, undesired respiratory secretions are prevented from flowing into the ventilation port or back toward the patient. Such secretions are squeegeed off of the external surface of the catheter during retraction.

The squeegee function is accomplished by a wiper seal snugly surrounding the catheter within the proximal end of the adaptor assembly. The wiper seal has two primary functions: to clean the external catheter wall during retraction so as to minimize practitioner exposure to patient contaminants; and to maintain a pressure seal around the catheter, ensuring a continuous closed, leak fight ventilation circuit. The preferred wiper seal configuration interfaces with the catheter tube with low frictional resistance, facilitating facile catheter insertion.

A sputum collector compartment is located between the wiper seal and the base of the adaptor to accumulate the undesired secretions. The sputum collector or trap has three distinct functions. It retains the wiper seal between the wiper trap and the adaptor housing, it provide relief space to accept the seal in flexure and it acts as a catheter guide during insertion and retraction of the catheter.

Upon completion of an evacuation procedure, a practitioner retracts the catheter. In some arrangements, a structure, such as a flare at the distal tip of the catheter, catches against a trap wall narrowing in the catheter passageway within the introducer tip. This flare to trap wall contact further enhances and maintains the closed-system environment within the manifold by providing a positive stop which prevents a practitioner from inadvertently retracting a catheter from the manifold and catheter adaptor.

After the practitioner has performed the respiratory evacuation procedure, the introducer housing may be axially rotated in the direction opposite to the direction it was turned at the beginning of the procedure, thereby to decouple the adaptor assembly so that it can be retracted from the manifold.

As the adaptor assembly is being retracted from the manifold, the introducer housing maintains a closed-system seal, even as the introducer tip within is pulled through the directional barrier. After the aperture in the directional barrier is closed, thereby maintaining a pressure and sterility barrier, the introducer housing may be retracted proximally off from the manifold. The single use catheter and adaptor assembly may then be dropped onto the sterile field barrier atop the patient, together with the surgical gloves, and the sterile field may be wrapped around the gloves, catheter and adaptor assembly and discarded appropriately, leaving the closed-system, single-patient manifold in place for later multiple uses.

The first and second coupling structures of the introducer housing and manifold are adapted to axially rotate at a second position. With the distal tip of the suction catheter retracted within the introducer housing, the introducer housing may be axially rotated at the second station to effect a coupling or decoupling of the adaptor assembly and the manifold. When the manifold and introducer housing are coupled at the second position, a closed-system seal within the manifold is maintained; yet the introducer housing can be neither retracted proximally off from the manifold nor distally advanced through the aperture. With the adaptor assembly in the second position, the catheter assembly is removed and discarded and the adaptor assembly is situated for single-patient reuse with a series of new catheter assemblies until the sputum collector compartment accumulates sufficient undesired secretions or other contaminants to warrant its disposal. Accordingly, reuse of the adaptor assembly may achieve yet additional economies.

A dust cap, typically tethered to the manifold, may be placed over the proximal end of the manifold between suction procedures. The dust cap acts as a protective barrier between the suction procedures as well as a seal against pressure differentials across the manifold to prevent back flow through the normally closed directional barrier.

The invention contemplates an adaptor structured as an interface for related diagnostic and therapeutic procedures, such as bronchoscopies and introduction of nebulized medicaments. The interface is structured and functions essentially like the catheter adaptor. The entry of the interface may be sealed by an entry valve similar to that of a directional barrier of a manifold. The entry valve may be carried within a cylindrical extension of the interface. Alternatively the entry of the interface may be sealed by a cap tethered to the body of the manifold. The interface cap may be formed in the opposite side of the manifold dust cap.

A vacuum valve assembly of this invention typically comprises an elongate valve body with a window opening on one side, an occlusion member, a length of resilient, such as rubber, tubing carried within the valve body, a slide ring concentrically surrounding the valve body and a valve base coupling attached to the tubing at the distal end of the valve assembly. The occlusion member may be formed as a curved surface solid, typically a sphere, and is sized to fit within and move back and forth through the valve body window. The occlusion member is located within the window between the resilient tubing on the inside and the slide ring on the outside. The tubing constitutes a flow path which is selectively pinched shut or released to open by manipulating the position of the occlusion member.

The slide ring may be moved selectively between a fist, open, position and a second, closed, position. The ring is structured so that at its first (usually proximally retracted) position, a relief space is provided into which the occlusion member can be urged by the outward memory bias of the resilient tubing. In this position, the bias of the tubing naturally results in an unobstructed tubing lumen. The slide ting is tapered centrally inward to a smaller diameter so that in its second (usually distally advanced) position, the occlusion member is forced inward against the tubing, thereby effecting collapse of the tubing to occlude the lumen. To preclude inadvertent actuation, the vacuum valve assembly may be securely locked in this closed position by rotating the slide ring to engage mechanisms, such as threads, on the interior distal surface of the slide ting with corresponding coupling mechanisms, such as complementary threads, on the exterior proximal surface of the valve base coupling.

A proximal wing coupling may be releasably attached to the valve base coupling. The attachment is preferably achieved with a press fit relation but may alternatively be achieved with a single or multiple-lead threaded relation or post and groove relation similar to that embodied by the first and second coupling structures of the manifold and the introducer housing. A similar releasable attachment may be effected between a distal wing coupling and the proximal end of the adaptor assembly or manifold.

It is significant that throughout the entirety of a respiratory evacuation procedure, a sterile, closed-system environment is maintained within the manifold. This invention thus makes it possible for such respiratory evacuation procedures to be accomplished without the need for assistance from ancillary personnel; an individual respiratory nurse or technician can perform the entire procedure alone.

A particular benefit of this invention is the capability of maintaining ongoing oxygenation or other ventilation of the patient throughout the entirety of a procedure, without the need for repeated disconnection, connection or other moving of ventilating tubes and other auxiliary equipment.

It is also significant that the manifold, comprising one of the more costly components of the invention, may be left unobtrusively attached to the patient in position for reuse for numerous additional suctioning procedures with single-use catheter and adaptor assemblies of relatively negligible expense. Similarly, a catheter adaptor may beneficially be reused for additional economies. The vacuum valve, which comprises another of the more costly components of this invention, is also reusable for numerous procedures involving one or more patients.

Of related significance is the capacity of this invention to afford its user latitude in selection of a mode of protection from contaminants on the external surface of a single-patient, single-use suctioning catheter. This invention further affords a practitioner flexibility for alternative diagnostic and therapeutic procedures while maintaining a closed-system environment and positive end expiratory pressure within the manifold.

BRIEF DESCRIPTION OF THE ILLUSTRATED EMBODIMENTS

In the drawings, which illustrate what is currently regarded as the best mode for carrying out the invention:

FIG. 11 is a view in cross section of a double end dust cap of a preferred embodiment; and FIG. 12 is a view in cross section of an alternative adaptor component of the invention.

DETAILED DESCRIPTION OF THE ILLUSTRATED EMBODIMENTS

Figure 1:
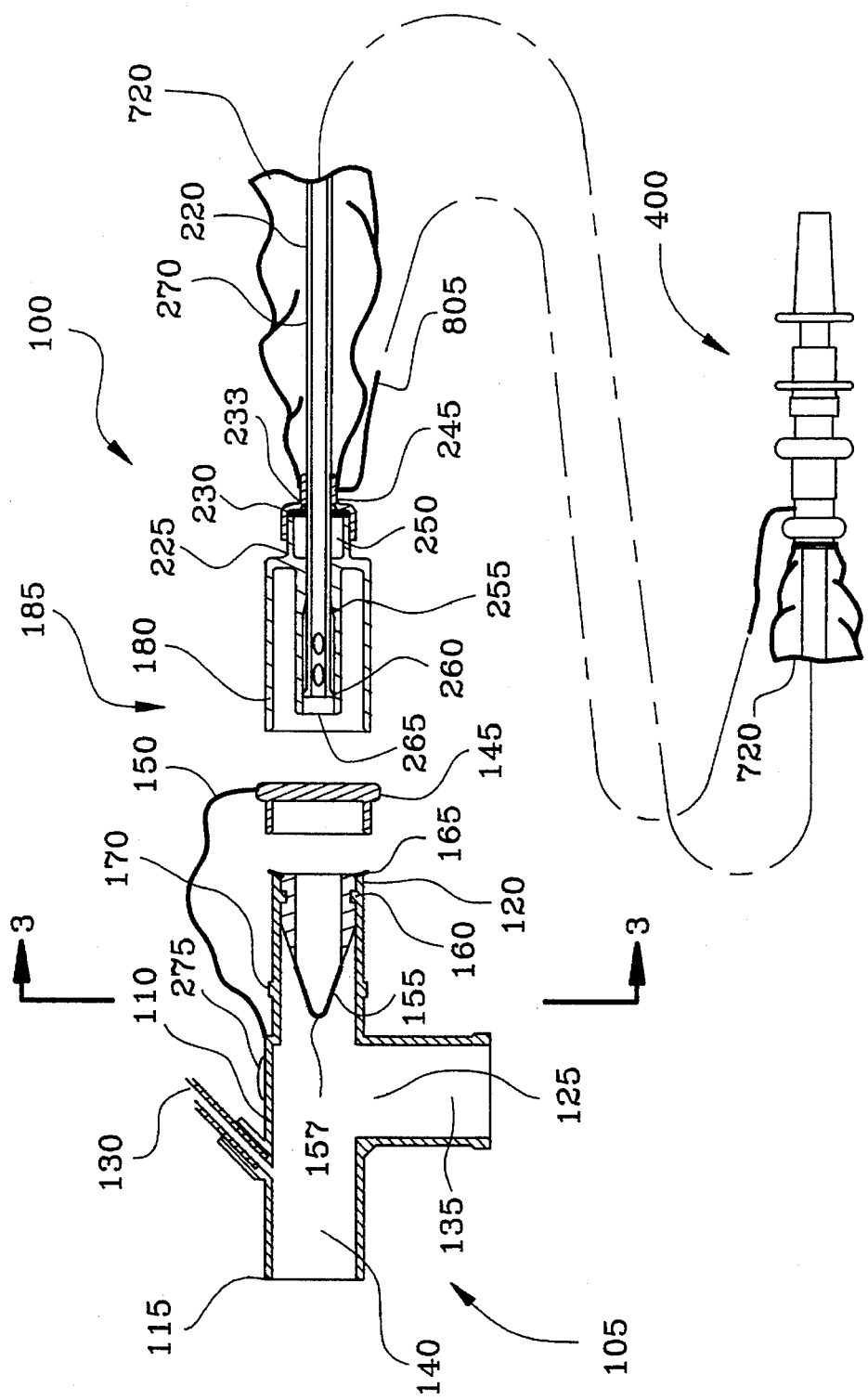
FIG. 1 is a partially exploded and partially broken away cross-sectional view in elevation of a preferred embodiment of the invention in disassembled condition.
Figure 2:
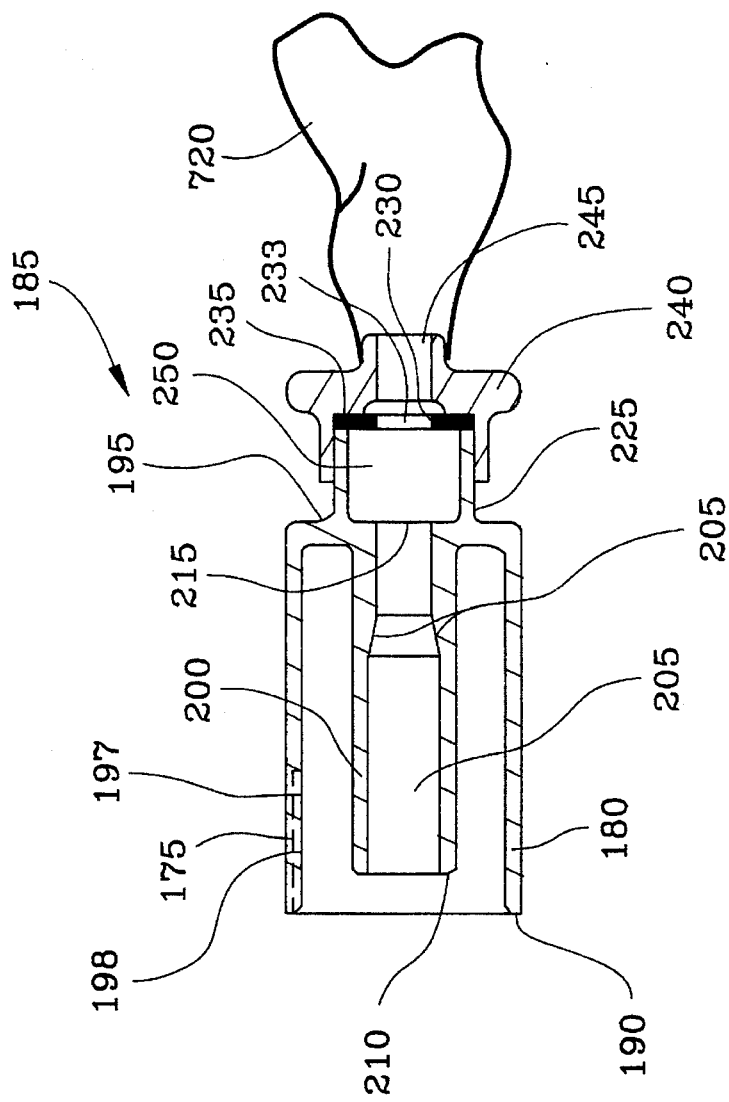
FIG. 2 is an enlargement of a portion of FIG. 1.
Figure 3:
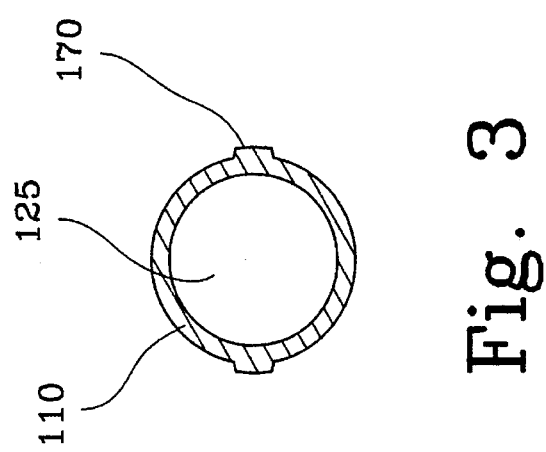
FIG. 3 is a view in elevation, taken on the reference line 3–3 of FIG. 1.

FIGS. 1–4, illustrate one configuration of a device, designated generally 100, embodying the invention. A manifold assembly, designated generally 105, comprises a body 110 with a distal end 115 and a proximal end 120. The body 110 defines a space 125 between the distal end 115 and proximal end 120. A lavage port 130 located on the body 110 of the manifold assembly 105 opens into and is in communication with the manifold space 125. Similarly, a ventilation port 135 located on the body 110 is in communication with the manifold space 125. Located at the distal end 115 of the body 110 is an endotracheal port 140 opening toward the patient and attachable to an indwelling fixture (not shown), such as a tracheal, endotracheal or nasopharyngeal tube.

A cap 145, capable of coveting the proximal end 120 of the body 110, may be attached to the body 110 with a tether 150. Situated within the space 125 of the body 110 is a directional barrier 155, preferably formed of a pliant, durable, rubber-like material with strong dimensional memory. The directional barrier 155 includes a central aperture 157, and is seated around its entire cross-sectional periphery against a rim 160 extending inwardly from the internal wall of the body 110. The barrier 155 and the rim 160 interface in a manner that achieves a sealing and anchoring of the directional barrier 155 relative to the body 110. A seal extension 165 may protrude slightly from the directional barrier 155 axially beyond the proximal end 120 of the body 110 to provide additional sealing effect between the cap 145 and the body 110 when the cap 145 is in position to cover the proximal end 120 of the body 110.

At least one positioning and locking post 170 extends radially outward from the body 110 of the manifold assembly 105. The post 170 interacts with a locking channel 175 formed in the internal wall of an introducer housing 180 of a catheter adaptor 185, as illustrated more clearly in FIG. 2. The channel 175 extends axially from the adaptor front 190 in the direction of the adaptor base 195, providing relative axial positioning of the manifold assembly 105 and the catheter adaptor 185. The channel 175 continues radially at approximately a fight angle from its initial axial direction at a first position 197, providing a means of locking the manifold assembly 105 and the catheter adaptor 185 together when the post 170 has been moved axially to the position 197, and is then turned radially within the channel 175. A second transverse extension from the channel 175 may be provided at a second position 198 as well as means for locking the assembly 105 and adaptor 185 together at an extended position. The seal extension 165 is shown configured to seal against the internal wall of the introducer housing 180 as the catheter adaptor 185 and manifold assembly 105 are in the process of being assembled. The seal extension 165 is further structured to seal against the adaptor base 195 when the catheter adaptor 185 is locked to the manifold assembly 105. In this attached position, the resilience of the seal extension 165 biases the adaptor 185 axially to maintain locking pressure between the locking post 170 of the manifold assembly 105 and the first transverse extension 197 of the channel 175 of the introducer housing 180.

The catheter adaptor 185 comprises an introducer tip 200 situated concentric with and inside of the introducer housing 180. The introducer tip 200 is seated against, and may be formed integrally with the adaptor base 195. A catheter passageway 205 is formed through the length of the introducer tip 200, opening at the leading edge 210 and through a catheter opening 215 in the adaptor base 195. The catheter opening 215 may be formed with a cross-sectional dimension slightly larger than but corresponding to the outside cross-sectional dimension of a tracheal suctioning catheter 220.

Trap walls 225 extend axially from, and are formed integrally with, the adaptor base 195. A pliant and resilient washer-like wiper seal 230 with a hole 233 therethrough is placed against the distal edge 235 of the trap walls 225. A distal wing coupling 240 is releasably attached to the trap walls 225 and may be structured and arranged to hold the wiper seal 230 in place. The distal wing coupling 240 includes a support opening 245 which provides catheter guidance and relief of strain on the catheter 220 imposed by non-axial forces encountered during insertion and retraction of the catheter 220. In combination, the wiper seal 230, the distal wing coupling 240 and the trap wall 225 contribute to the sterility and pressure barrier function of the manifold 185 during use. The trap walls 225 together with the wiper seal 230 define a sputum collector 250.

Upon retraction of the catheter 220, sputum, phlegm and other undesired respiratory secretions are squeegeed from the external surface of the catheter 220 by the wiper seal 230. The diameter of the hole 233 is desirably sized slightly smaller than the outer diameter of the catheter 220 to facilitate this function. These undesired respiratory liquids are then directed into the sputum collector 250 where they are retained from leakage back toward the patient or out toward the respiratory practitioner. If the practitioner is equipped with protective hand ware and the patient is covered by a sterile field barrier under the retracted catheter 220, adequate protection from cross-contamination may be achieved without additional precautions.

The catheter passageway 205 narrows at a reducing constructor 255 near the catheter opening 215. A flare 260 at the catheter nozzle 265 catches against the reducing constructor 255 upon retraction of the catheter 220. Alternatively, a notch 267 catches against the wiper seal 230 or the constructor 255 upon retraction of the catheter 220.

Figure 4:
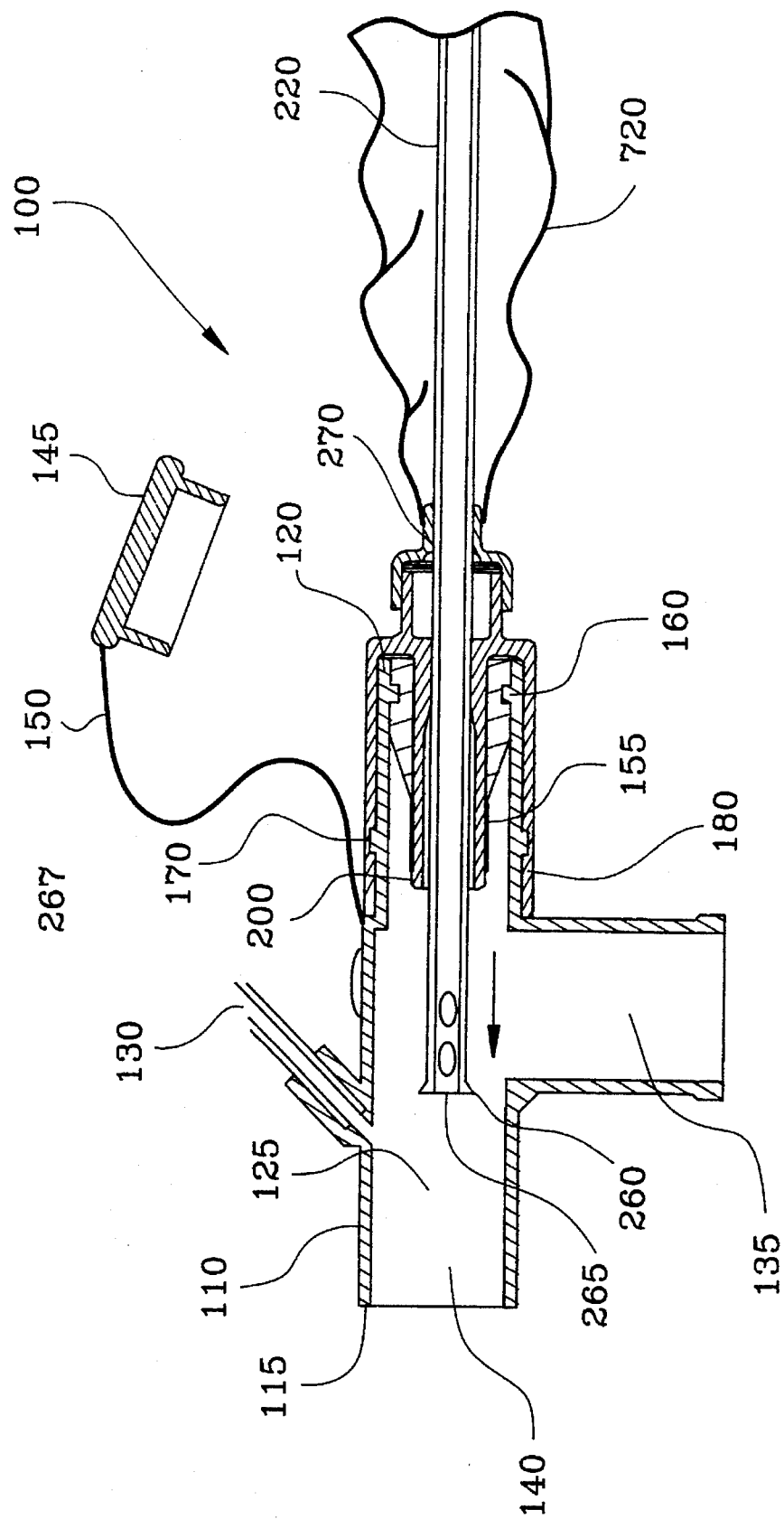
FIG. 4 is a view similar in part to FIG. 1, but showing the components in assembled condition.

As best shown by FIG. 4, the device 100 and its respective components allow a respiratory practitioner to maintain a closed-system within the single-patient, multiple use manifold assembly 105 throughout attachment of the catheter adaptor 185 to the manifold assembly 105, evacuation of a medical patient through ambidextrous actuation of vacuum pressure, retraction of the tracheal catheter 220 and detachment of the single-use, disposable catheter adaptor 185. The practitioner may then, with minimal waste and cost, discard the catheter 220 and adaptor structure 185 and place the cap 145 over the proximal end 120 of the manifold assembly 105 until next use, leaving no partially obstructed catheter, plastic envelope and complicated valve structure to interfere with other procedures and auxiliary equipment.

The catheter 220 may carry indicia 270 at various locations along its sidewall. These indicia, as well as the catheter nozzle 265, are visible through the wall of the manifold body 110, portions of which may be configured as a lens 275. The lens 275 structure may be incorporated in the body 110 during an injection molding process, for example, if the body is formed from a transparent moldable material. The indicia provide a convenient means for monitoring the precise location of the catheter nozzle 265 during a procedure.

Figure 5:
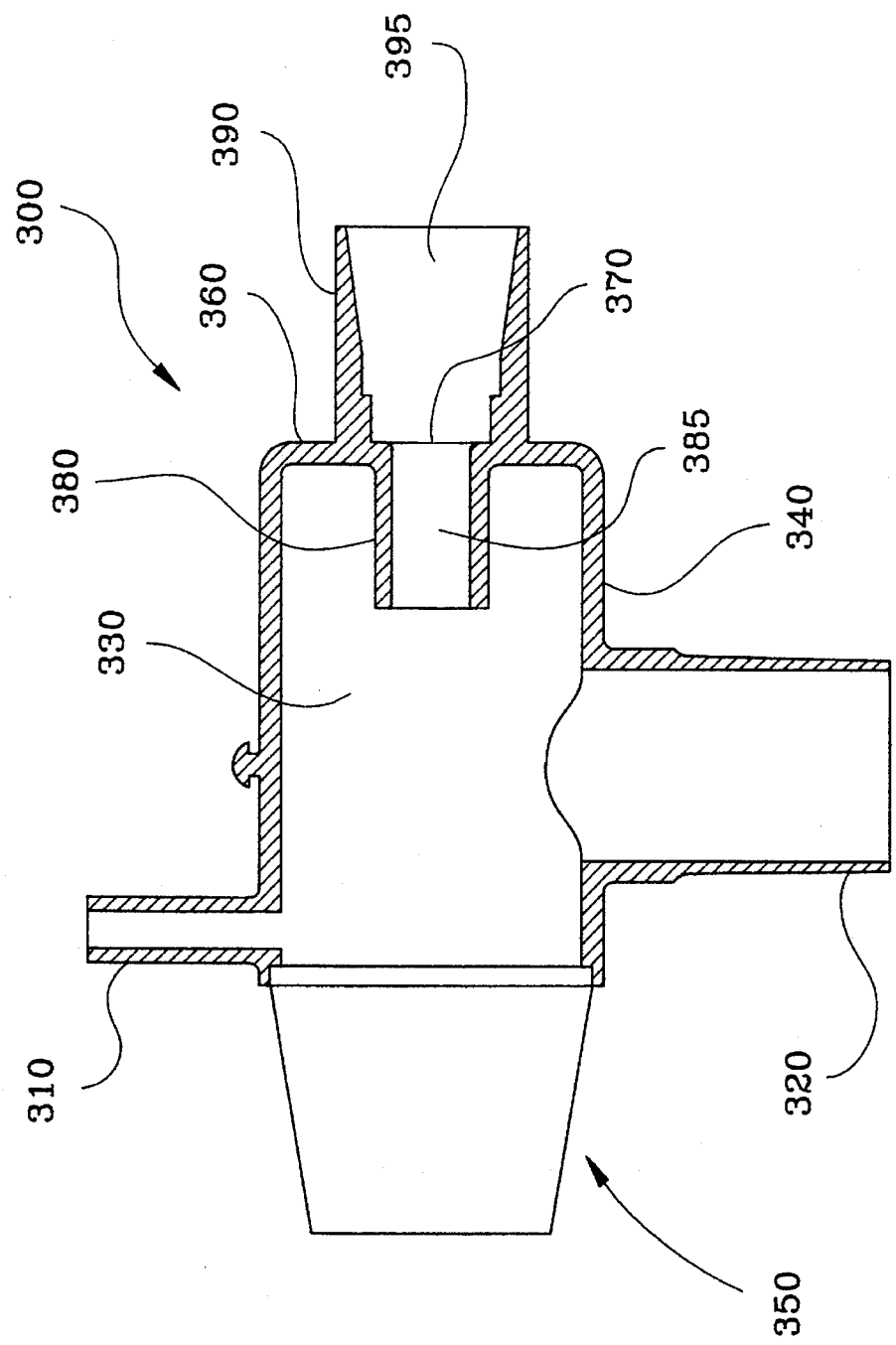
FIG. 5 is a cross-sectional view of a portion of an alternative embodiment of a component of the invention.

An alternative manifold 300 depicted in FIG. 5 is structured and adapted for lower cost and for instances not involving the need to maintain positive end expiratory pressure within the manifold 300. As illustrated, this embodiment is characterized by modular flexibility, and includes a lavage port 310 and a ventilating port 320, each in communication with the space 330 defined by the body 340. Proximal anchoring structure, depicted generally as 350, constitutes means for releasable attachment to an indwelling endotracheal tube (not shown).

The manifold 300 further comprises a base 360 with an opening 370 through which the standard tracheal catheter 220 can be inserted into and through the space 330. Positioned on the base 360 and essentially concentric with the opening 370 and the body 340 is a catheter guide 380 defining a guide space 385 through which the catheter 220 is inserted and within which the catheter 220 is supported by the catheter guide 380 during a suctioning procedure. A manifold receptacle 390 defines a receptacle space 295 into which a bare catheter 220 can be inserted by a gloved user or onto which a distal wing coupling 240 can be releasably attached.

Figure 6:
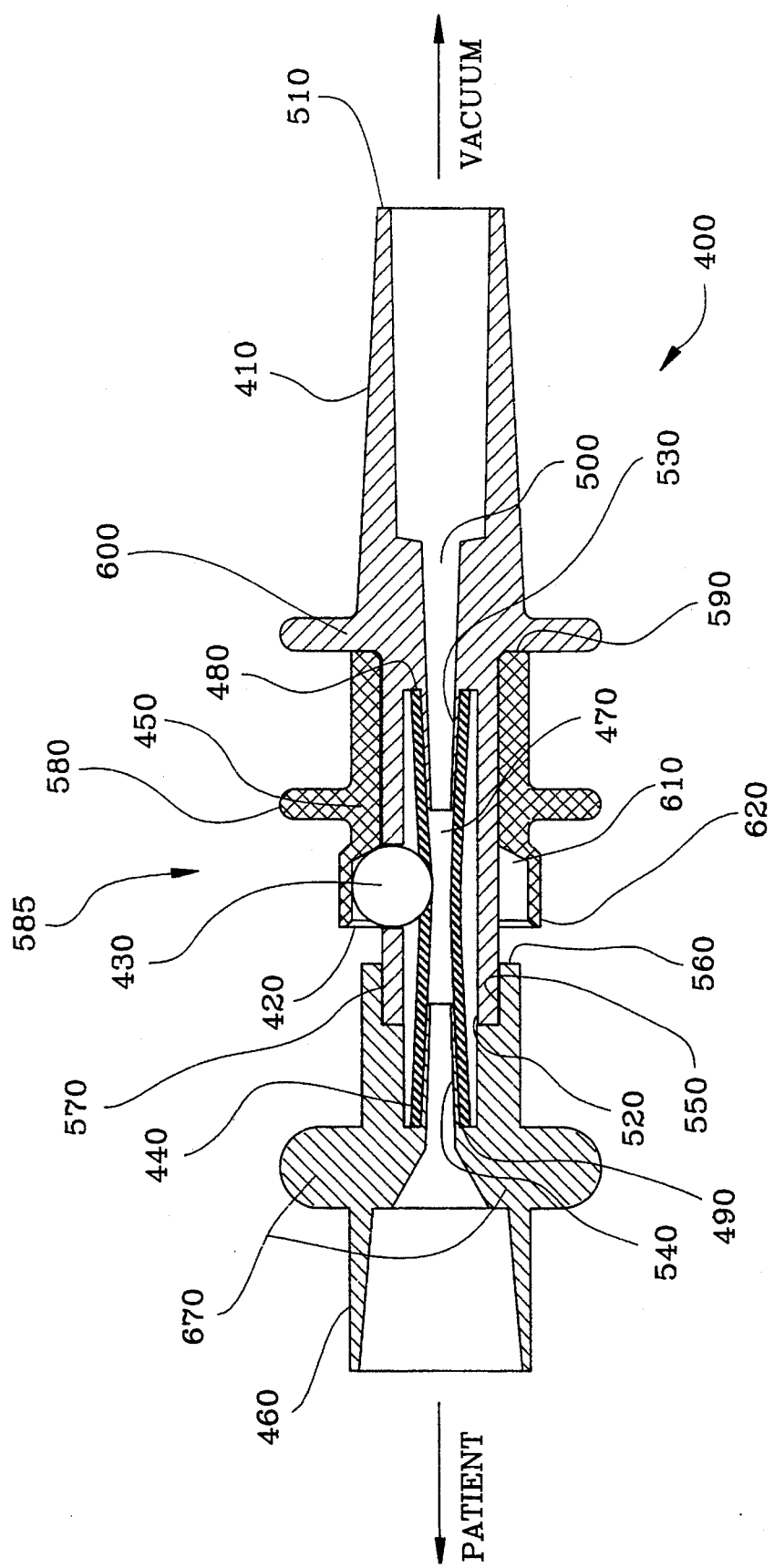
FIG. 6 is a cross-sectional view of a valve component of a preferred embodiment of the invention showing certain elements in a first positional arrangement.
Figure 7:
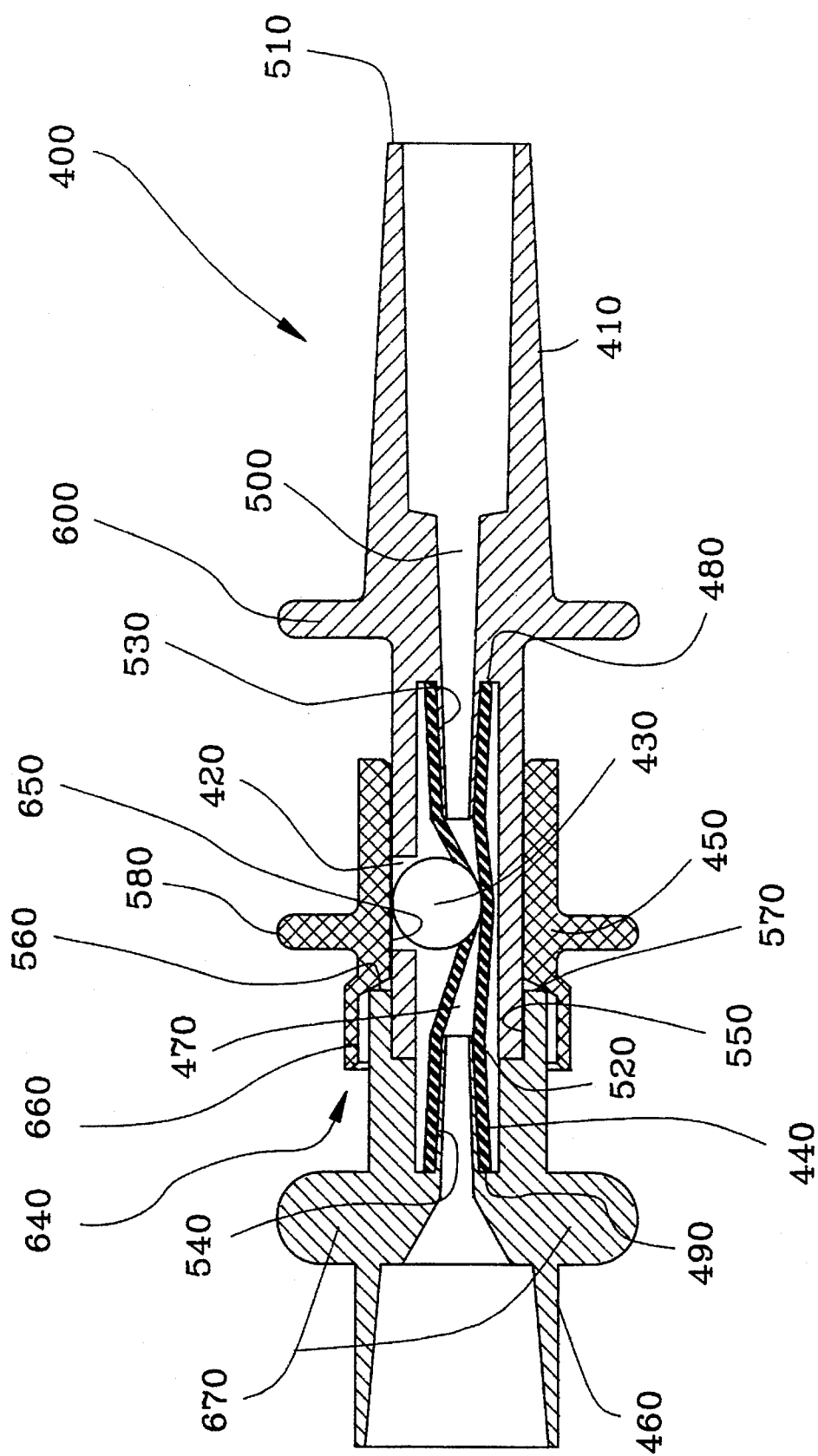
FIG. 7 is a view similar to FIG. 6, but depicting the elements in a second positional arrangement.

A vacuum valve assembly, generally 400 in FIGS. 6 and 7, comprises a valve body 410 with a side window 420, a sphere-shaped occlusion member 430, an elongate resilient but collapsible tube 440, a slide ting 450 and a valve base 460. The tube 440 defines a lumen 470 opening at a proximal lumen end 480 and a distal lumen end 490. The valve body 410 defines a body space 500 opening at a vacuum end 510 and an actuation end 520. The vacuum end 510 is removably but snugly inserted into a conduit which is in communication with a vacuum source (not shown). The tube 440 is carried within the valve body 410 and is anchored at its proximal opening 480 to a body stump 530 and at its distal opening 490 to a base stump 540. The valve base 460 is similarly bonded or welded at the inner wall 550 of its valve end 560 to the outer wall 570 of the actuation end 520 of the valve body 410.

The slide ring 450 may incorporate a radially outwardly projecting flange 580 to enhance the grip of a user. When the slide ting 450 is moved to a proximally retracted station 585, as portrayed generally in FIG. 6, its user end 590 abuts a positive stop 600 extending outward from the valve body 410. The positive stop 600 is preferably formed to extend radially outward as a further enhancement to the grip of a user. Thus, manual pressure is applied by the user to the positive stop 600 in an axial direction opposite to the direction of manual axial movement of the slide ring 450. While at its retracted station 585, the widening annular flare 610 defined by the leading edge 620 of the slide ting 450 accommodates movement of the occlusion member 430 radially outward through the window 420 of the valve body 410 in response to the outward bias of the tube 440.

At an advanced station 630, as generally portrayed in FIG. 7, the annular flare 610 receives, and the leading edge 620 of the slide ring 450 circumscribes, the valve end 560 of the valve base 460. Accordingly, at the advanced station 630, the inner wall 650 of the slide ring 450, having a smaller relative cross-sectional dimension than that of the leading edge 620, holds the occlusion member 430 radially inward; the tube 440 is pinched by the occlusion member 430; and the tube lumen 470 is thereby obstructed. In the embodiment illustrated by FIG. 7, the slide ring 450 may be rotated and thereby locked at the advanced station 630 by complimentary threads 660 on the leading edge 620 and the valve end 560, respectively.

Figure 8:
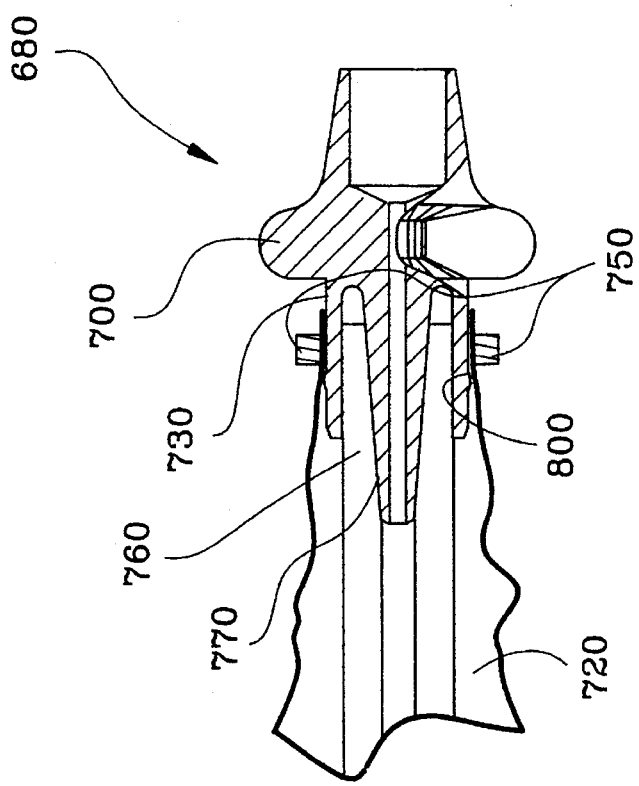
FIG. 8 is a cross-section cut away view of a coupling element of a preferred embodiment.
Figure 10:
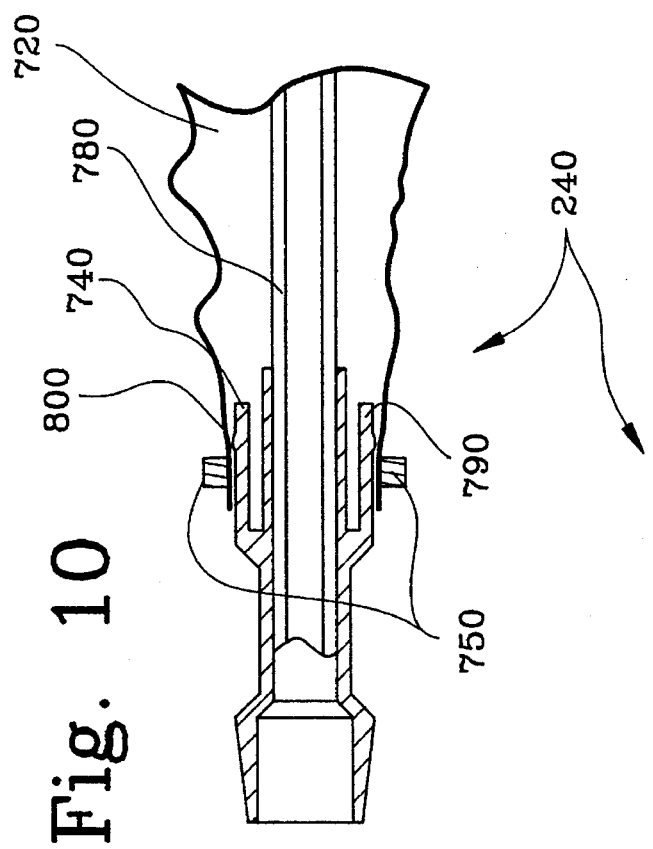
FIG. 10 is a view similar in part to FIG. 9, but showing the coupling element rotated axially 90 degrees.
Figure 9:
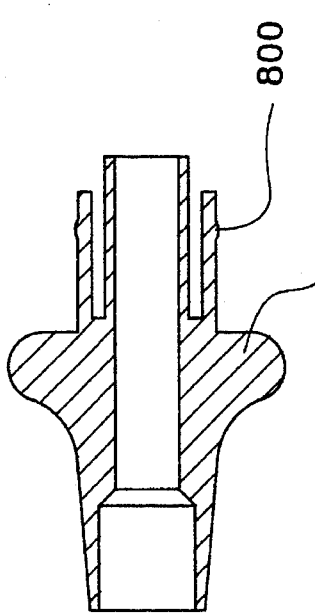
FIG. 9 is a cross-section view of another portion of a preferred embodiment.

The valve base 460 comprises at least one, but preferably two, tabs 670 extending radially outward for facilitating releasable attachment of a proximal wing coupling 680, shown in FIG. 8, to the valve base 460. The proximal wing coupling 680 comprises wings 700 like the wings 710 of the distal wing coupling 240 illustrated most clearly in FIGS. 2 and 9.

Though a user may wear only gloves as protection while manipulating the contaminated exterior surface of a catheter 220, in the preferred embodiment a collapsible bag 720 envelopes the catheter 220. The catheter 220 is manually manipulated by collapsing the bag 720 onto the catheter 220 to advance or retract it.

The bag 720 is preferably sealed to the case 730 of the proximal wing coupling 680 or the reverse case 740 of the distal wing coupling 240 by tape, a shrink band or a molded band 750. The catheter 220 is attached at its proximal end 760 to the stub 770 of the proximal wing coupling 680 and at its distal end 780 to the reverse stub 790 of the distal wing coupling 240. The tape or band 750 holds the bag 720 against a raised relief protuberance or rim 800 formed around the case 730 as well as the reverse case 740.

In the illustrated embodiment (FIG. 1), a lanyard 805 is connected parallel the bag 720 between anchoring structures associated with the adaptor 185 and valve 400. The proximal 680 and distal 240 couplings constitute suitable such structures. The lanyard 805 functions to limit stretching of the bag 720, thereby preventing inadvertent excessive withdrawal of the catheter 220. For purposes of illustration, the lanyard 805 is illustrated external and separated from the bag 720. Alternative embodiments position the lanyard within the bag 720 or fixed, as by adhesive, to the inner or outer surface of the bag 720. A lanyard 805 may be also be provided in embodiments which omit the bag 720.

It is within contemplation that a catheter 220 may in some instances be withdrawn from the assembly (FIG. 1), leaving an adaptor 185 in place. An alternative form of the dust cap 145 shown in FIG. 1 is illustrated by FIG. 11. The alternative cap 810 may also be connected to a manifold 105 with the tether 150, and includes an open cylindrical extension 815, which accommodates the trap wall 225 (FIG. 1), in effect replacing the wiper seal 230 structure with a sealing cap 820. An enlarged portion 825 is dimensionally equivalent to the cap 145 so that the cap 810 may also function as a dust cap when the introducer housing is removed or is otherwise not present. This cap embodiment 810 is particularly advantageous for use with appliance adaptors 850 of the type illustrated by FIG. 12.

FIG. 11 is drawn to an enlarged scale compared to FIG. 12. Nevertheless, it can be seen that the smaller cap element 820 may be pressed over the end 860 when the adaptor 850 is installed as shown at the distal end of a manifold body 110. When the adaptor 850 is removed, the cap element 825 may be placed over the end 120 of the manifold 105. A directional barrier 870 provides a sliding seal entry for instruments, such as bronchoscopes, in a manner similar to that described in connection with catheter adapters.

The present invention may be embodied in other specific forms. The described embodiments are to be considered in all respects only as illustrative, and not restrictive. The scope of the invention is, therefore, indicated by the appended claims, which are intended to embrace the illustrated embodiments and all equivalents.

What is claimed is:

1. In combination, for use in patient ventilation and aspiration circuits:
    a manifold assembly, having a body with a distal end portion, a proximal end portion and an open interior;
    said distal end portion of said body being adapted to couple with an intubation device, said proximal end portion of said body being formed as an open port defined by a continuous wall, said proximal end portion further being approximately axially aligned with said distal end portion so that a catheter may be inserted through said proximal end portion to exit from said distal end portion;

structural means for associating a catheter with said proximal end; and a catheter assembly comprising:
  a flexible tracheal suctioning catheter tube attached at a first end to a proximal coupling and at a second end opposite said first end to a distal coupling,
    said proximal coupling being structurally adapted releasably to connect to first connecting structure associated with a vacuum valve, and
    said distal coupling being structurally adapted releasably to connect to second connecting structure associated with said manifold assembly;
  said vacuum valve comprising:
    a flow channel defined by a continuous flexible wall; and
    associated actuation structure being arranged for selective positive, finger-actuated, adjustment between a first position and a second position, said actuation structure being constructed and arranged such that in said first position said actuation structure presses said flexible wall to occlude said flow channel and in said second position said actuation structure releases said flexible wall to open said flow channel;
  a collapsible bag formed of stretchable material enveloping said suctioning catheter tube and attached at opposite ends to said proximal and distal couplings; and
  a lanyard element connected in parallel with said bag between said proximal and distal couplings, said lanyard limiting the axial separation of said couplings, said lanyard being adhered directly to a wall forming said bag.

2. A combination according to claim 1, wherein said manifold assembly includes a directional barrier configured to be inserted in said proximal end portion of said body in sealing relationship with said open interior, said barrier comprising a normally closed valving structure; and said structural means comprises:
  a catheter adaptor, including:
    a leading end portion adapted to couple with said proximal end portion; and
    a trailing end portion carrying a catheter introducer structure, said introducer structure being constructed and arranged to interface with said directional barrier when said leading end portion is coupled with said proximal end portion.

3. A combination according to claim 1 wherein said lanyard is contained within said collapsible bag.

4. A combination according to claim 1 wherein said actuation structure is constructed and arranged to remain in either of said first and second positions until it is deliberately adjusted to a different position.

5. A combination according to claim 4 wherein said vacuum valve comprises:

a vane body with a hollow interior;

an occlusion member positioned at least partially within said hollow interior; and an elongate resilient but collapsible tube comprising said flow channel extending through said hollow interior in contact with said occlusion member;

wherein said actuation structure is operable selectively to urge said occlusion member into engagement with said tube, whereby to collapse said tube to close said flow channel and out of engagement with said tube, whereby to permit said tube to assume its uncollapsed condition with said flow channel open.

6. A combination according to claim 5, wherein said occlusion member is situated within a window opening from exterior said valve body into said hollow interior so that it is free to move within said window transverse said tube; and said actuation structure comprises an engagement member slidably mounted to said valve body for reciprocal movement between said first and second positions;

said window, occlusion member and engagement member being mutually structured and arranged so that:
  movement of said engagement member into said first position urges said occlusion member to move within said window transversely against said tube, effecting closure of said flow channel,
  and movement of said engagement member into said second position provides a relief space adjacent said window, permitting the natural resilient memory of said tube to urge said occlusion member into said window, effecting opening of said flow channel.

7. A combination according to claim 6, wherein said valve body includes an approximately cylindrical portion, containing said window, adjacent a base portion;

said actuation structure is formed as an approximately annular ring structure reciprocally mounted with respect to said approximately cylindrical portion;

said base portion and said ring structure carrying first and second elements, respectively, of a coupling mechanism operable to lock said actuation structure into said first position.

8. In combination, for use in patient ventilation and aspiration circuits:

a manifold assembly, having a body with a distal end portion, a proximal end portion and an open interior;
  said distal end portion of said body being adapted to couple with an intubation device,
  said proximal end portion of said body being formed as an open port defined by a continuous wall, said proximal end portion further being approximately axially aligned with said distal end portion so that a catheter may be inserted through said proximal end portion to exit from said distal end portion; and a catheter assembly comprising:
  a flexible tracheal suctioning catheter tube attached at a first end to a proximal coupling and at a second end opposite said first end to a distal coupling,
    said proximal coupling being structurally adapted releasably to connect to a vacuum valve, and
    said distal coupling being structurally adapted releasably to connect to said manifold assembly;
  a collapsible bag formed of stretchable material enveloping said suctioning catheter tube and attached at opposite ends to said proximal and distal couplings; and
  a lanyard element connected in parallel with said bag between said proximal and distal couplings, said lanyard limiting the axial separation of said couplings, said lanyard being adhered directly to a wall forming said bag.

9. A combination according to claim 8, wherein said manifold assembly includes a directional barrier configured to be inserted in said proximal end portion of said body in sealing relationship with said open interior and comprises a normally closed valve seal structure.

10. A combination according to claim 8, wherein said lanyard is contained within said collapsible bag.

11. A combination according to claim 8, wherein said manifold assembly includes a ventilation port in fluid flow communication with said open interior, said ventilation port having a central axis transverse the central axes of said proximal end portion and said distal end portion.

12. A combination according to claim 11, wherein said manifold assembly includes a lavage port in fluid flow communication with said open interior, said lavage port having a central axis transverse said central axes of said proximal end portion and said distal end portion.

13. A combination according to claim 8 wherein at least one of said proximal and distal couplings carries structure engageable by human fingers, whereby to facilitate finger actuation for releasably connecting said coupling to a corresponding connecting structure.

14. A combination according to claim 13 wherein a said coupling includes a body portion of generally non-cylindrical cross sectional configuration.

15. A combination according to claim 14 wherein said cross sectional configuration effects an external winged configuration for said coupling.

16. A combination according to claim 8, including an appliance adaptor comprising:

a leading end portion adapted to couple with said proximal end portion of said manifold; and a trailing end portion constituting an interface including an entry for the introduction of medical appliances into a trachea through said manifold, said entry being sealed by a directional barrier.

17. A combination according to claim 16, wherein said directional barrier is carried within a cylindrical extension of said interface.

18. A combination according to claim 17, including a dust cap member having:

a first resilient element with a closed top and a first approximately cylindrical side wall 1 dimensioned to effect a press fit cover for said proximal end portion of said manifold; and a second resilient element comprising a second approximately cylindrical side wall extending from said closed top opposite said first side wall dimensioned to effect a press fit cover for said trailing end portion of said adaptor.

* * * * *

UNITED STATES PATENT AND TRADEMARK OFFICE
CERTIFICATE OF CORRECTION

Page 1 of 2

PATENT NO. : 5,598,840
DATED : February 4, 1997
INVENTOR(S) : Iund et al.

It is certified that error appears in the above-indentified patent and that said Letters Patent is hereby corrected as shown below:

In column 1, line 16, change "option" to --operation--;

In column 1, line 19, after "source" insert --to--therefore;

In column 1, line 29, change "close-system" to --closed system--;

In column 2, line 42, change "dement" to --element--;

In column 2, line 55, change "robe" to --tube--;

In column 2, line 62, change "vane" to --valve--;

In column 5, line 14, change "fight" to --right--;

In column 6, line 22, change "fight" to --tight--;

In column 7, line 51, change "ting" to --ring--;

In column 7, line 58, change "ting" to --ring--;

In column 9, line 17, change "coveting" to --covering--;

In column 9, line 42, change "fight" to --right--;

In column 11, line 22, change "ting" to --ring--;

In column 11, line 46, change "ting" to --ring--;

UNITED STATES PATENT AND TRADEMARK OFFICE
CERTIFICATE OF CORRECTION

PATENT NO. : 5,598,840
DATED : February 4, 1997
INVENTOR(S) : Iund, et. al.

It is certified that error appears in the above-identified patent and that said Letters Patent is hereby corrected as shown below:

In column 13, line 63, change "vane" to --valve--.

Signed and Sealed this

Sixteenth Day of December, 1997

Attest:

Attesting Officer

BRUCE LEHMAN

Commissioner of Patents and Trademarks